United States Patent [19]

Lang et al.

[11] 4,098,882
[45] Jul. 4, 1978

[54] ANTI-SOLAR COMPOSITION

[75] Inventors: Gérard Lang, Epinay-sur-Seine; Bernard Jacquet, Antony, both of France

[73] Assignee: L'Oreal, Paris, France

[21] Appl. No.: 617,158

[22] Filed: Sep. 26, 1975

[30] Foreign Application Priority Data

Sep. 26, 1974 [LU] Luxembourg ............... 71012

[51] Int. Cl.² .................... A61K 7/42; C07D 311/02
[52] U.S. Cl. ........................ 424/59; 260/274; 424/47; 424/63; 424/64; 424/174
[58] Field of Search ............ 424/59, 47; 260/274

[56] References Cited

U.S. PATENT DOCUMENTS

| | | | |
|---|---|---|---|
| 2,334,348 | 11/1943 | Miglaresee | 424/59 |
| 2,921,078 | 1/1960 | Boehme | 424/59 X |
| 3,178,459 | 4/1965 | Pike | 424/59 |

FOREIGN PATENT DOCUMENTS 1,114,030  5/1973  United Kingdom ............... 424/59

Primary Examiner—Dale R. Ore
Attorney, Agent, or Firm—Cushman, Darby & Cushman

[57] ABSTRACT

Anti-solar cosmetic composition containing as the protective agent against actinic rays a compound of the formula

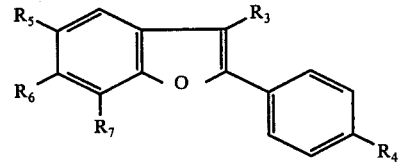

wherein $R_3$ is hydrogen, $-COR_1$ or $-CHOHR_1$ wherein $R_1$ is $CH_3$ and $R_4$, $R_5$, $R_6$ and $R_7$ each independently represent hydrogen or $-OR_2$ wherein $R_2$ is lower alkyl containing 1-4 carbon atoms.

9 Claims, No Drawings

ANTI-SOLAR COMPOSITION

The present invention relates to anti-solar compositions containing certain derivatives of 2-phenyl benzofurane.

It is known that 2-phenyl benzofurane and certain of its methyl derivatives, principally those methylated at the 5, 6, 7, 2' and 4' positions thereof have been employed is cosmetic compositions as a filtering agent for ultra-violet rays, as indicated in British patent specification No. 1,114,030. These compounds are said to be effective in the absorption zone of erythematous rays.

The present invention has for an object the provision of cosmetic compositions capable of retarding the development of solar erythema without, however, inhibiting the pigmentation of the skin which, in addition to its aesthetic appearance, provides a natural protection against harmful solar rays.

It is well known that solar rays reaching the surface of the earth can be classified into 3 types of radiation: ultra-violet rays, visible rays and infra-red rays. Ultra-violet rays, which are the most energetic, are the source of solar erythema and can cause, if exposition to such rays is prolonged, serious burns, and even skin cancer.

In effect, the ultra-violet flux itself decomposes to erythematous flux (wave lengths between 290 and 320 nm) causing the appearance of erythema which can occur, generally in a period of about 2–5 days, thus providing a natural pigmentation due to photo-induced melanogenesis, and on the other hand, into a non-erythematous bronzing flux (wave lengths between 320 and 370 nm) causing an immediate pigmentation which can occur in a period of about 2–5 hours after the initial exposure to the ultra-violet rays due to a photo-oxidation of certain precursors of melanine present in the skin.

Obviously then it is desirable to be able to retard the appearance of solar erythema and its development into burns, and thus permit a longer or more intense exposition to ultra-violet rays without interfering with the beneficial contribution of natural bronzing also provided by exposure to such rays.

The present invention thus relates to an anti-solar composition which provides the above advantages and which comprises in a cosmetic vehicle capable of forming a continuous film which is easily spaced on the skin, a protective agent against actinic rays, said agent comprising at least one compound having the formula:

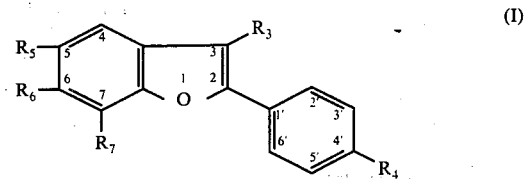

wherein $R_3$ is hydrogen, $-COR_1$ or $-CHOHR_1$ wherein $R_1$ is methyl, and $R_4$, $R_5$, $R_6$ and $R_7$ each independently represent hydrogen or $-OR_2$ wherein $R_2$ is lower alkyl having 1–4 carbon atoms. The said protective agent is present in the anti-solar composition of this invention in an amount ranging from 0.05 to 10 weight percent, and preferably from 0.5 to 6 weight percent, of said composition.

The compounds of formula I exhibit excellent absorption of the ultra-violet rays in the range of wave lengths of 290 to 320 nm (nonometer) as indicated by the rapid diminution of the ratio, (transmitted erythematous flux)/(incident erythematous flux) or % $\phi_E^T$ as a function of the concentration of said agent in the composition as well as the choice of the solvent and components contained therein. The anti-solar compositions of the present invention assure the protection of the skin by absorbing erythematous rays when said composition is in the form of a film having a thickness generally between 3 and 20 microns on said skin. The selection of any particular compound of formula (I) and of the concentration thereof in the composition as well as the selection of a particular cosmetic vehicle, provides a means for tailoring the composition of the invention to produce effective protection for various types of skin.

The above stated ratio advantageously provides a direct indication of the degree of protection against erythematous rays for a given concentration of said agent in the composition and a given solvent or a cosmetic vehicle, as indicated by B. M. Cumperlik, in J. Soc. Cosmet. Chem, 23, page 333, 1972.

The table below indicates, for a certain number of the compounds of formula I and for various concentrations C expressed in milligrams per 100 ml of methanol, on the one hand the value of the ration $\phi_E^T$ expressed in % and, on the other hand, the value of the ratio (transmitted non-erythematous bronzing flux)/(incident non-erythematous bronzing flux), represented by $\phi_{BNE}^T$. Each of the measurements reported was effected in an analysis cell through a thickness of 10 mm of a solution of the composition.

| | Compound | % $\phi_E^T$ (Concentration C in mg/100 ml of methanol) | | | | % $\phi_{BNE}^T$ (Concentration C in mg/100 ml of methanol) | | | |
|---|---|---|---|---|---|---|---|---|---|
| No | Formula | 1 | 2 | 3 | 4 | 1 | 2 | 3 | 4 |
| 1 | ![benzofuran with OCH3 groups] | 10.18 | 1.09 | 0.14 | 0.03 | 55.27 | 47.26 | 44.12 | 42.11 |

-continued

| No | Compound Formula | % $\phi_E^T$ (Concentration C in mg/100 ml of methanol) | | | | % $\phi_{BNE}^T$ (Concentration C in mg/100 ml of methanol) | | | |
|---|---|---|---|---|---|---|---|---|---|
| | | 1 | 2 | 3 | 4 | 1 | 2 | 3 | 4 |
| 2 | benzofuran-2-yl-(4-methoxyphenyl) | 4.83 | 0.85 | 0.49 | 0.38 | 72.21 | 64.92 | 61.57 | 53.30 |
| 3 | 3-acetyl-7-methoxy-2-(4-methoxyphenyl)benzofuran | 32.13 | 10.37 | 3.36 | 1.10 | 55.11 | 36.11 | 22.68 | 15.29 |
| 4 | 3-acetyl-2-(4-methoxyphenyl)benzofuran | 30.47 | 9.33 | 2.87 | 0.89 | 52.05 | 30.73 | 20.29 | 14.59 |
| 5 | 7-methoxy-2-phenylbenzofuran | 16.76 | 5.36 | 3.28 | 2.65 | 94.84 | 90.70 | 87.36 | 84.61 |
| 6 | 3-(1-hydroxyethyl)-2-(4-methoxyphenyl)benzofuran | 16.24 | 4.69 | 2.56 | 1.96 | 93.70 | 88.75 | 84.79 | 81.57 |
| 7 | 3-(1-hydroxyethyl)-7-methoxy-2-(4-methoxyphenyl)benzofuran | 18.16 | 3.64 | 0.88 | 0.30 | 74.71 | 63.73 | 58.06 | 54.65 |
| 8 | 3-(1-hydroxyethyl)-2-(4-methoxyphenyl)benzofuran (isomer) | 23.19 | 7.35 | 3.52 | 2.31 | 92.68 | 86.88 | 82.21 | 78.40 |
| 9 | 3-(1-hydroxyethyl)-5-methoxy-2-(4-methoxyphenyl)benzofuran | 18.93 | 3.84 | 1.08 | 0.47 | 59.00 | 38.78 | 28.09 | 21.95 |
| 10 | 3-acetyl-7-methoxy-2-(4-methoxyphenyl)benzofuran | 46.6 | 21.87 | 10.33 | 4.91 | 60.89 | 83.53 | 33.82 | 27.50 |

-continued

| Compound | | % $\phi_E^T$ (Concentration C in mg/100 ml of methanol) | | | | % $\phi_{BNE}^T$ (Concentration C in mg/100 ml of methanol) | | | |
|---|---|---|---|---|---|---|---|---|---|
| No | Formula | 1 | 2 | 3 | 4 | 1 | 2 | 3 | 4 |
| 11 | ![structure] | 28.33 | 8.92 | 3.46 | 1.81 | 79.56 | 69.98 | 64.27 | 60.27 |
| 12 | ![structure] | 10.81 | 1.39 | 0.31 | 0.14 | 69.02 | 59.35 | 55.02 | 52.44 |

By employing a method similar to that used for the determination of the percentage of transmitted erythematous flux, $\phi_E^T$, by the protective agent of the present invention in the wave length range of 290 to 340 nm, the percentage of the transmitted immediate or non-erythematous bronzing flux, $\phi_{BNE}^T$, by these same protective agents in the wave length range of 320 to 375 nm can also be determined.

It is well known that anti-solar compositions have been formulated, on the one hand to take into account the sensitivity of the skin to be protected and on the other hand, to take into account the intensity or length of exposure of the skin to solar rays. Thus, according to the particular type of formulation desired, a protective agent exhibiting an appropriate value of % $\phi_E^T$ or % $\phi_{BNE}^T$ must be selected.

Thus, for the protection of very sensitive skin which is allergic to the sun, a composition employing a protective agent having very weak % $\phi_E^T$ and % $\phi_{BNE}^T$ is used. On the other hand, bronzing compositions for use on sensitive skin utilize a protective agent having a % $\phi_E^T$ value as weak as possible and a % $\phi_{BNE}^T$ value as strong as possible.

The compounds of formula I whose dermal toxicity is very weak have a satisfactory to good solubility in solvents or fatty products. Thus there can be employed in the compositions of the present invention, as cosmetic adjuvants, lanolin, petrolatum, glycerin, triglycerides of fatty acids, polyethylene glycols, oxyethylenated fatty alcohols, fatty esters such as isopropyl palmitate, myristate or stearate, oleyl oleate, butyl stearate, animal, vegetable or mineral oils, fatty alcohols, glycerol monostearate, organic and mineral waxes or a mixture thereof, present, respectively, in an amount of 1–97, 5 weight percent of said composition. The isopropyl palmitate or myristate is particularly appropriate for the preparation of compositions susceptible of being applied to the skin in the form of a continuous film and having a desired thickness thereon.

The compounds of formula I can be employed in a hydro-alcoholic or oleo alcoholic cosmetic vehicle or even in an aerosol composition.

The compounds of formula I are present in the anti-solar compositions of the invention in an amount of 0.5 to 6 weight percent relative to the weight of the composition and preferably from 1 to 5 weight percent. The compositions of this invention can be provided in the form of lotions, solar oils or emulsions, aerosols, gels, dispersions or suspensions.

The present invention also relates to compounds of the formula:

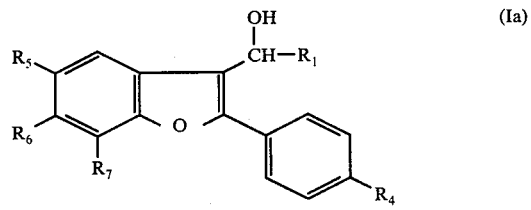

(Ia)

wherein $R_1$, $R_4$, $R_5$, $R_6$ and $R_7$ have the meanings given above. These compounds can be prepared by a known four-stage process, represented by the following reaction scheme:

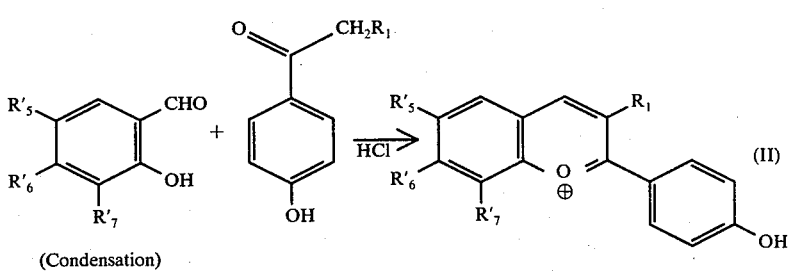

(Condensation)

-continued

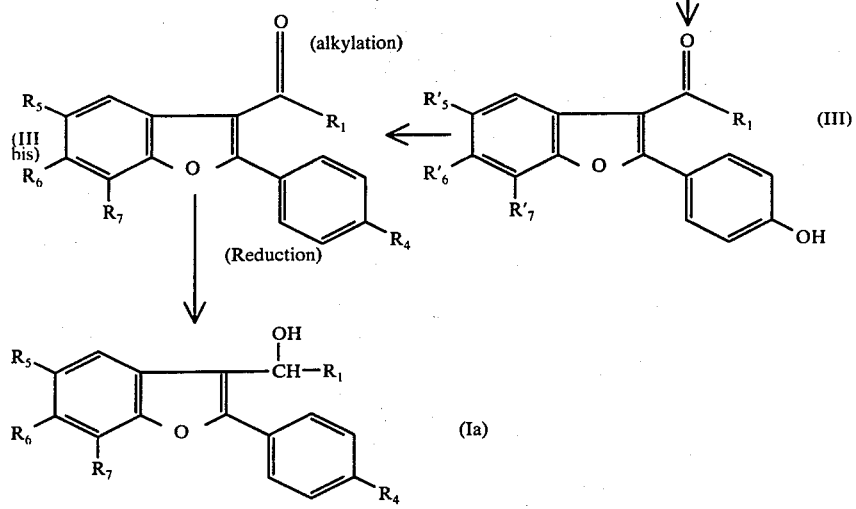

wherein $R_1$, $R_4$, $R_5$, $R_6$ and $R_7$ have the values given above and $R'_5$, $R'_6$ and $R'_7$ each independently represent H, $-OR_2$ or OH wherein $R_2$ has the meaning given above.

As can be seen this process includes a condensation stage (1) which produces flavylium salts (II); an oxidation stage (2) which produces compounds of formula (III); an alkylation state (3) which produces compounds of formula (III bis); and a reduction stage (4) which produces compounds of formula (Ia). The reduction stage is effected using either sodium borohydride in the presence of an alcohol containing 1–4 carbon atoms or a double hydride of lithium and aluminum in suspension in an inert solvent such as sulfuric ether, isopropyl ether or tetrahydrofuran.

The compounds of formula I in which $R_3$ is hydrogen can be prepared by a process known as cyclodehydration in the presence of polyphosphoric acid from an aryloxyacetophenone of the formula

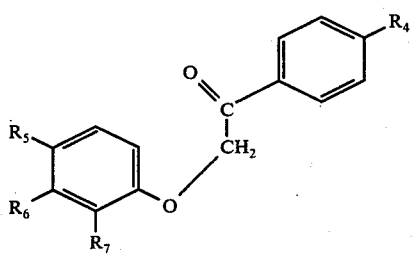

(IV)

wherein $R_4$, $R_5$, $R_6$ and $R_7$ have the meanings given above.

This well known process comprises heating for a period of time and at a temperature which can vary depending on the initial aryloxyacetophenone selected, a mixture of said aryloxyacetophenone and polyphosphoric acid in a respective weight proportion of about 1:10. This reaction is accompanied by a rearrangement giving as the cyclization product a 2-aryl benzofurane.

The invention also relates to an improved process for the cyclodehydration of the compounds of formula IV to obtain the compounds of formula I wherein $R_3$ is hydrogen. According to this improved process, the aryloxyacetophenone of formula IV in an inert solvent such as xylene or toluene is heated, with agitation, at reflux in the presence of polyphosphoric acid used in an amount varying from ½ to 1/10 of the amounts conventionally employed.

This process provides numerous advantages relative to conventional procedures. It provides higher yields. Further, since the reaction occurs in a heterogeneous phase, the progression of the reaction can be more easily monitored by chromatographic or spectral analysis of a sample carried out in a supernatant organic layer. Moreover, the product obtained at the end of the reaction is more easily isolated.

In effect, as soon as the analytic controls indicate the end of the reaction, the upper organic layer of the reaction mixture can be separated. Subsequently, if desired, the lower phase can be extracted by again heating it, with agitation, together with an equal quantity of solvent initially employed in the reaction. Thereafter the resulting supernatant layer is separated and combined with the previously separated upper layer. The combined organic layers are then concentrated and the desired product is isolated either by crystallization, or by distillation under vacuum of the concentrated residue.

The following non-limiting examples are provided to illustrate the invention. Unless otherwise indicated, all parts and percentages are by weight and all temperatures are in degrees centigrade.

I — Preparation of Protective Agents

A. Preparation of derivatives of 2-phenyl benzofurane unsubstituted in the 3-position and having the formula

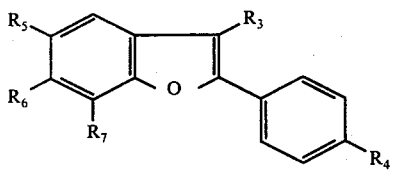

wherein $R_4$, $R_5$, $R_6$ and $R_7$ can have the values given for the compound of formula I.

General Method of Operation 182 g of phosphoric anhydride are added to 130 cm³ of phosphoric acid (d = 1.7), the addition being carried out in portions in order to avoid strong exothermicity. After the last addition, the resulting mixture is maintained free from moisture and with good agitation for 30 minutes at 130° C. There is then added a solution previously heated to reflux and dehydrated, containing an aryloxy acetophenone, from 80 to 400 g, in a quantity at least equal to 1 liter of xylene. The resulting mixture is then heated to reflux for 5 hours with good agitation. After cooling, the xylenic layer is separated and the lower phase is again heated with about 500 ml of xylene with agitation for 15 minutes. The resulting supernatant xylenic wash or extraction layer is separated from the polyphosphoric acid layer and is combined with the previously removed upper xylenic layer. After concentrating the previously dried xylenic layers, the residue is crystallized in ethanol, thus providing, principally, compounds 1, 2, 5, 11 and 12 indicated in Table A below, which also reports operating conditions, the melting point, F, of the resulting product and the yield obtained, Rdt.

TABLE A

| No | $R_4$ | $R_5$ | $R_6$ | $R_7$ | Time of Heating | Polyphosphoric acid weight / Aryloxyaceto phene weight | F (° C) | Rdt (%) |
|----|-------|-------|-------|-------|-----------------|--------------------------------------------------------|---------|---------|
| 5  | H     | H     | H     | OCH₃  | 5 h             | 2                                                      | 85°     | 65      |
| 12 | H     | OCH₃  | H     | H     | 5 h             | 4                                                      | 127°    | 60      |
| 2  | OCH₃  | H     | H     | H     | 5 h             | 2                                                      | 151°    | 58      |
| 1  | OCH₃  | OCH₃  | H     | H     | 5 h             | 2                                                      | 163°    | 48      |
| 11 | OCH₃  | H     | H     | OCH₃  | 5 h             | 2                                                      | 78°     | 15      |

B. Preparation of derivatives of 2-phenyl benzofurane substituted in the 3 position by an acyl radical and having the formula

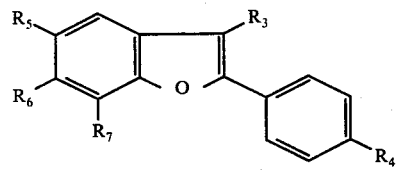

wherein $R_4$, $R_5$, $R_6$ and $R_7$ can have the values indicated for the compound of formula I and $R_3$ is acyl.

(a) A solution containing 152 g (1 mole) of orthovanilin and 150 g (1 mole) of para hydroxypropiophenone in 1 liter of ethyl acetate and 250 cm³ of absolute ethanol is saturated with gaseous HCl while cooling the whole in an ice bath. The resulting reaction mixture is left to stand for 12 hours at which time the precipitate which has formed is filtered, washed with ethyl acetate and air-dried.

(b) 300 g of the flavylium salt (formula II) resulting from step (a) above are dissolved in a mixture containing 3000 cm³ of methanol and 3000 cm³ of a buffer solution of pH 5.8. To the resulting mixture there are added 600 cm³ of H₂O₂ (30% by weight). The resulting reaction mixture which becomes colorless and in which a precipitate forms is left to stand for 1 hour at which time it is diluted with 5 liters of water with agitation. The precipitate is then filtered off, washed with water, dried and crystallized in methanol, yielding 185 g of 3-acetyl-(4'-hydroxy phenyl)-2-methoxy-benzofurane (formula III) having a melting point of 222° C.

(c) A mixture containing 183 g of the compound resulting from step (b), 366 g of anhydrous potassium carbonate and 183 cm³ of methyl sulfate in 3660 cm³ of anhydrous acetone is heated at reflux for 3 hours while maintaining good agitation. After cooling the mineral salts are separated therefrom by filtration and the remaining filtrate is concentrated. The resulting concentrated residue is treated with a dilute aqueous solution of potassium carbonate and is stirred until a precipitate forms. The precipitate is then separated by filtration, washed with water, dried and crystallized in methanol, yielding 136 g of 3-acetyl-7-methoxy-2-(4'-methoxy phenyl) benzofurane (III bis), having a melting point of 98° C. The yield is 70%.

Elemental analysis (compound No. 3)—$C_{18}H_{16}O_4$

|         | % C   | % H  |
|---------|-------|------|
| Theory  | 73.0  | 5.44 |
| Found   | 73.05 | 5.62 |

By operating in a similar manner, the compounds indicated in Table B below are prepared, the said Table also reporting the melting point, F, of each compound and the yield obtained.

TABLE B

| No   | $R_3$  | $R_4$ | $R_5$ | $R_6$ | $R_7$ | F(° C) | Yield (%) |
|------|--------|-------|-------|-------|-------|--------|-----------|
| (9)* | COCH₃  | OCH₃  | OCH₃  | H     | H     | 115    | 90        |
| 10   | COCH₃  | OCH₃  | H     | OCH₃  | H     | 77     | 89        |
| 4    | COCH₃  | OCH₃  | H     | H     | H     | 73     | 85        |

Elemental analysis effected on compounds Nos. 4 and 10 provided the following results:

|                         | % C            | % H            |
|-------------------------|----------------|----------------|
| No. 4 ($C_{17}H_{14}O_3$) | Theory 76.7   | Theory 5.26    |
|                         | Found 76.51    | Found 5.25     |
| No. 10 ($C_{18}H_{16}O_4$) | Theory 73.0 | Theory 5.44    |
|                         | Found 73.10    | Found 5.45     |

C. Preparation of 3-(α-hydroxy alkyl)-2-aryl benzofurane having the formula

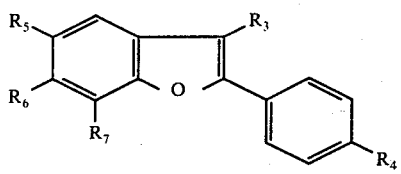

wherein $R_4$, $R_5$, $R_6$ and $R_7$ have the values indicated for the compound of formula (I) and $R_3$ is α-hydroxy alkyl.

Preparation of 3-α-hydroxyethyl-7-methoxy-2-(4'-methoxy phenyl) benzofurane.

To a solution containing 75 g of 3-acetyl-7-methoxy-2-(4'-methoxy phenyl) benzofurane (III bis) in 400 cc of methanol there is slowly added a solution containing 17.5 g of sodium borohydride in 200 cc of methanol. The resulting mixture is heated at reflux, with agitation, for 5 hours. The solvent is removed and the residue is then taken up in 200 cm³ of water, with agitation. The precipitate which forms is then separated by filtration, washed thoroughly with water, and crystallized in alcohol, yielding 54 g of 3-(α-hydroxy ethyl)-7-methoxy-2-(4'-methoxy phenyl) benzofurane (Ia) having a melting point of 100° C. The yield is 72%.

Elemental analysis (Compound No. 8 — $C_{18}H_{18}O_4$).

|  | % C | % H |
|---|---|---|
| Theory | 72.6 | 6.05 |
| Found | 72.75 | 6.29 |

This is a new compound.

By operating in a similar manner, the compounds indicated in Table C below are prepared, Table C also reporting the melting point, F, of each compound and the yield obtained.

TABLE C

| No. | $R_3$ | $R_4$ | $R_5$ | $R_6$ | $R_7$ | F(° C) | Yield (%) |
|---|---|---|---|---|---|---|---|
| 6 | CHOHCH₃ | OCH₃ | H | H | H | 78° | 80 |
| 9 | CHOHCH₃ | OCH₃ | OCH₃ | H | H | 60° | 75 |
| 7 | CHOHCH₃ | OCH₃ | H | OCH₃ | H | 98° | 93 |

Elemental analysis effected on compounds 6, 7 and 9 provides the following results:

| | % C | | % H | |
| Compound | Theory | Found | Theory | Found |
|---|---|---|---|---|
| No. 6 ($C_{17}H_{16}O_3$) | 76.2 | 76.13 | 5.98 | 5.86 |
| No. 7 ($C_{18}H_{18}O_4$) | 72.6 | 72.62 | 6.05 | 6.24 |
| No. 9 ($C_{18}H_{18}O_4$) | 72.6 | 72.51 | 6.05 | 6.12 |

Compounds 6, 7 and 9 of Table C are new.

Examples of Anti-Solar Compositions

EXAMPLE 1

| Anti-solar oil | |
|---|---|
| Compound No. 7 | 2 g |
| Perfume | 0.5 g |
| Di-tertiary-butyl paracresol | 0.0625 g |
| Colza oil, q.s.p. | 100 g |

Similarly effective anti-solar oils are prepared by replacing compound No. 7 in the above with an essentially equal amount of Compounds Nos. 4, 6 or 8.

EXAMPLE 2

| Anti-solar lotion | |
|---|---|
| Propyl gallate | 0.0625 g |
| Triglycerides of $C_8-C_{12}$ fatty acids | 40 g |
| Compound No. 6 | 3 g |
| Benzyl salicylate | 4 g |
| Ethyl alcohol - 96° titer, q.s.p. | 100 g |

Similarly effective anti-solar lotions are prepared by replacing compound No. 6 in the above with an essentially equal amount of Compounds Nos. 4, 7 or 8.

EXAMPLE 3

| Anti-solar aerosol oil | |
|---|---|
| Absolute ethyl alcohol | 32 g |
| Isopropyl myristate | 23 g |
| Ricin oil | 2 g |
| Perfume | 1 g |
| Compound No. 4 | 2 g |
| Dichlorodifluoromethane | 40 g |

Similarly effective anti-solar aerosol oils are prepared by replacing Compound No. 4 in the above with an essentially equal amount of compounds Nos. 6, 7 or 8.

EXAMPLE 4

| Anti-solar aerosol foam | |
|---|---|
| Stearic acid | 1 g |
| Triglycerides of $C_8-C_{12}$ fatty acids | 50 g |
| Oleyl alcohol | 2 g |
| Triethanolamine | 1 g |
| Crosslinked polyacrylic acid | 0.5 g |
| Perfume | 0.5 g |
| Propyl parahydroxy benzoate | 0.3 g |
| Compound No. 8 | 2 g |
| Water, q.s.p. | 100 g |

90 g of the above described mixture are packaged in an aerosol container under pressure together with 10 g dichlorodifluoromethane.

Similarly effective anti-solar aerosol foams are prepared by replacing compound No. 8 in the above with an essentially equivalent amount of compounds Nos. 4, 6 or 7.

EXAMPLE 5

| Softening and filter spray | |
|---|---|
| Cocoa butter | 10 g |
| Compound No. 1 | 2 g |
| Isopropyl myristate | 25 g |
| Nordihydroguaiaretic acid, "NDGA", sold by Roche | 0.005 g |
| Perfume | 0.8 g |
| Triglycerides of $C_8-C_{12}$ fatty acids, q.s.p. | 100 g |

50 g of this composition are packaged in an aerosol container under pressure together with 30 g of Freon 12 (dichlorodifluoromethane) and 20 g of Freon 114 (dichlorotetrafluoroethane).

Similarly effective sprays can be prepared by replacing compound No. 1 in the above with an essentially equal amount of compounds Nos. 4, 6, 7, 8 or 12.

EXAMPLE 6

| Anhydrous anti-solar gel | |
|---|---|
| Petrolatum - Codex | 45 g |
| Petrolatum oil - Codex | 25 g |
| Vinyl polystearate | 5 g |
| Microcrystalline wax | 10 g |
| Lanolin | 2 g |
| Propyl gallate | 0.05 g |
| Peanut oil | 10 g |
| Perfume | 0.8 g |
| Compound No. 12 | 2 g |

Similarly effective gels can be prepared by replacing compound 12 in the above with an essentially equal amount of compounds Nos. 1, 4, 6, 7 or 8. Further a fat soluble dye can be incorporated into the above compositions.

EXAMPLE 7

| Anti-solar cream for dry skin | |
|---|---|
| Triglycerides of $C_8$-$C_{12}$ fatty acids | 30 g |
| Glycerol monostearate | 6 g |
| Stearic acid | 2 g |
| Cetyl alcohol | 1.2 g |
| Lanolin | 4 g |
| Silicone oil | 1 g |
| Methyl parahydroxy benzoate | 0.3 g |
| Propylene glycol | 2 g |
| Triethanolamine | 0.5 g |
| Compound No. 7 | 3 g |
| Perfume | 0.5 g |
| Water, q.s.p. | 100 g |

Similarly effective creams are prepared by replacing compound No. 7 in the above with an essentially equal amount of compounds Nos. 1, 4, 6, 8 or 12.

EXAMPLE 8

| Anti-solar cream for normal skin | |
|---|---|
| Cetyl stearyl alcohol oxyethylenated with 9 moles of ethylene oxide | 2 g |
| Glycerol monostearate | 4 g |
| Cetyl alcohol | 4 g |
| Vaseline oil | 10 g |
| Isopropyl myristate | 5 g |
| Propylene glycol | 7 g |
| Natural polysaccharide thickening agent | 0.5 g |
| Butyl parahydroxy benzoate | 0.3 g |
| Perfume | 0.4 g |
| Compound No. 6 | 2.5 g |
| Water, q.s.p. | 100 g |

Similarly effective creams are prepared by replacing compound No. 6 in the above with an essentially equal amount of compounds Nos. 1, 4, 7, 8 or 12.

EXAMPLE 9

| Anti-solar milk for normal skin | |
|---|---|
| Oleyl cetyl alcohol oxyethylenated with 25 moles of ethylene oxide | 5 g |
| Petrolatum oil | 6 g |
| Isopropyl myristate | 3 g |
| Silicone oil | 1 g |
| Cetyl alcohol | 1 g |
| Glycerine | 20 g |
| Methyl parahydroxy benzoate | 0.3 g |
| Perfume | 0.3 g |
| Compound No. 7 | 1.5 g |

| Anti-solar milk for normal skin (continued) | |
|---|---|
| Water, q.s.p. | 100 g |

Similarly effective anti-solar milks are prepared by replacing compound No. 7 in the above with an essentially equivalent amount of compounds Nos. 1, 4, 6, 8 or 12.

EXAMPLE 10

| Anti-solar lipstick | |
|---|---|
| Cocoa butter | 10 g |
| Ozokerite | 20 g |
| Compound No. 8 | 5 g |
| Paraffin | 4.9 g |
| Oleyl alcohol | 6 g |
| Ricin oil | 8 g |
| Propyl gallate | 0.05 g |
| Lanolin | 8 g |
| Titanium oxide | 2 g |
| Perfume | 0.5 g |
| Petrolatum oil - Codex, q.s.p. | 100 g |

Similarly effective anti-solar lipsticks can be prepared by replacing compound No. 8 in the above with an essentially equal amount of compounds Nos. 1, 4, 6, 7 or 12.

The perfumes used in Examples 1–10 above are those conventionally employed in anti-solar compositions.

What is claimed is:

1. An anti-solar cosmetic composition for application to human skin comprising a cosmetic vehicle easily spreadable on human skin to form a continuous film thereon, at least one protective agent against actinic rays, said agent having a formula selected from the group consisting of

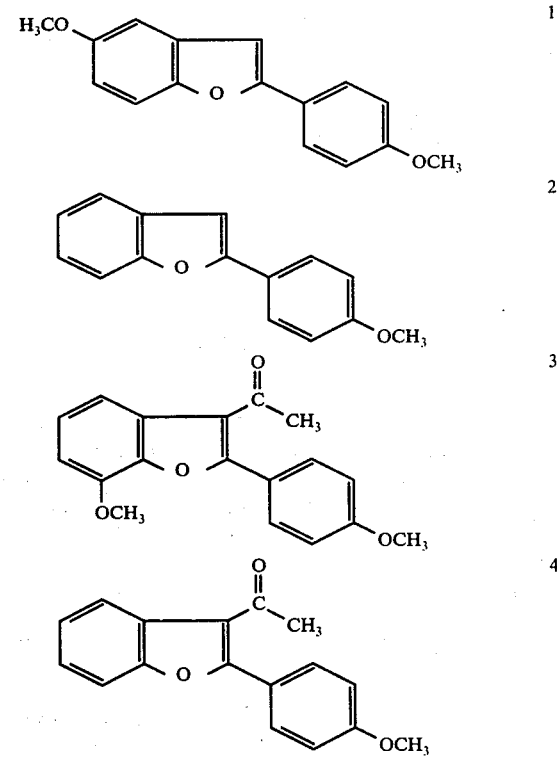

-continued

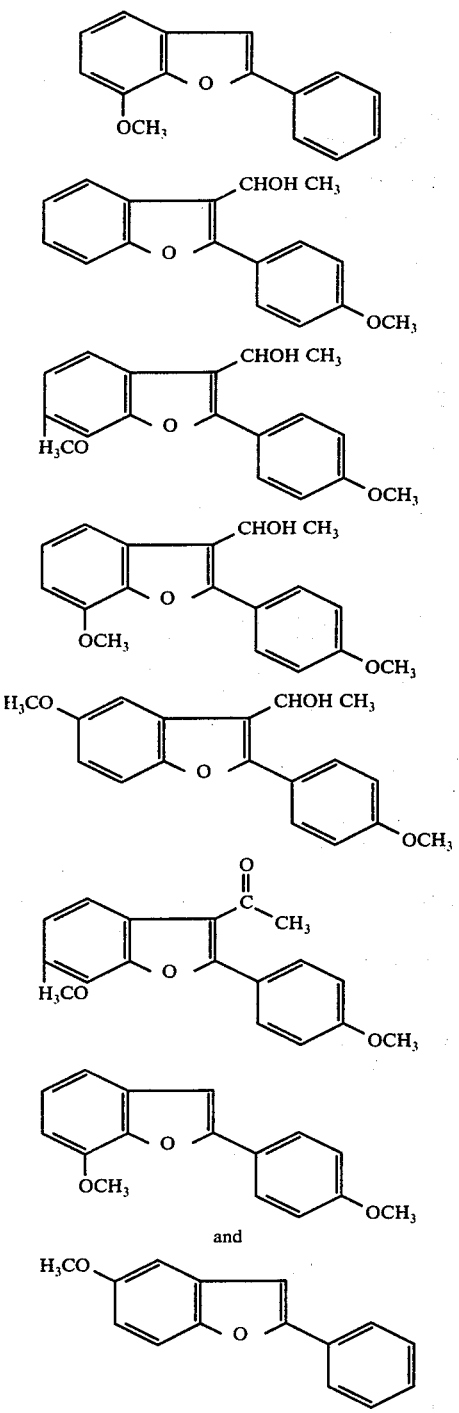

and said agent being present in an amount effective to protect said skin against actinic rays, said cosmetic vehicle being selected from the group consisting of water, a lower alcohol, a hydroalcoholic mixture, an oil selected from colza oil, cocoa butter, triglycerides of fatty acids containing eight to 12 carbon atoms, isopropyl myristate, petroleum oil, petrolatum; vinyl polystearate lanolin, ricin oil, paraffin and oleyl alcohol, and a wax selected from microcrystalline wax and ozokerite.

2. An anti-solar cosmetic composition for application to human skin comprising a cosmetic vehicle easily spreadable on human skin to form a continuous film thereon, at least one protective agent against actinic rays, said agent having the formula

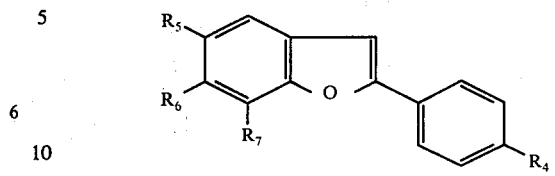

wherein $R_4$, $R_5$, $R_6$, and $R_7$ are sets of values selected from:

(a) $R_4$, $R_5$ and $R_6$ are hydrogen and $R_7$ is $OCH_3$,
(b) $R_4$, $R_6$ and $R_7$ are hydrogen and $R_5$ is $OCH_3$,
(c) $R_5$, $R_6$ and $R_7$ are hydrogen and $R_4$ is $OCH_3$,
(d) $R_4$ and $R_5$ are $OCH_3$ and $R_6$ and $R_7$ are hydrogen, and
(e) $R_4$ is $OCH_3$, $R_5$ and $R_6$ are hydrogen and $R_7$ is $OCH_3$, said agent being present in an amount effective to protect said skin against actinic rays, said cosmetic vehicle being selected from the group consisting of water, a lower alcohol, a hydroalcoholic mixture, an oil selected from colza oil, cocoa butter, triglycerides of fatty acids containing eight to 12 carbon atoms, isopropyl myristate, petroleum oil, petrolatum; vinyl polystearate lanolin, ricin oil, paraffin and oleyl alcohol, and a wax selected from microcrystalline wax and ozokerite.

3. An anti-solar cosmetic composition for application to human skin comprising a cosmetic vehicle easily spreadable on human skin to form a continuous film thereon, at least one protective agent against actinic rays, said agent having the formula

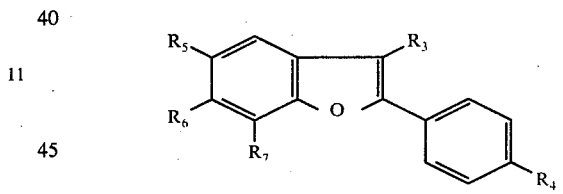

wherein $R_3$ is —$COCH_3$ and $R_4$, $R_5$, $R_6$ and $R_7$ each independently represent hydrogen or —$OR_2$ wherein $R_2$ is lower alkyl containing one to four carbon atoms, said agent being present in an amount effective to protect said skin against actinic rays, said cosmetic vehicle being selected from the group consisting of water, a lower alcohol, a hydroalcoholic mixture, an oil selected from the group consisting of colza oil, cocoa butter, triglycerides of fatty acids containing eight to 12 carbon atoms, isopropyl myristate, petroleum oil, petrolatum, vinyl polystearate; lanolin, ricin oil, paraffin and oleyl alcohol, and a wax selected from the group consisting of mycrocrystalline wax and ozokerite.

4. An anti-solar cosmetic composition for application to human skin comprising a cosmetic vehicle easily spreadable on human skin to form a continuous film thereon, at least one protective agent against actinic rays, said agent having the formula

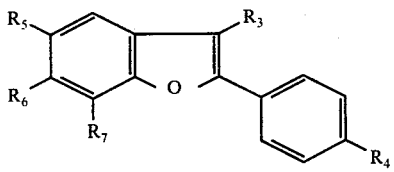

wherein $R_3$ is —CHOHCH$_3$ and $R_4$, $R_5$, $R_6$ and $R_7$ each independently represent hydrogen or —OR$_2$ wherein $R_2$ is lower alkyl containing one to four carbon atoms, said agent being present in an amount effective to protect said skin against actinic rays, said cosmetic vehicle being selected from the group consisting of water, a lower alcohol, a hydroalcoholic mixture, an oil selected from the group consisting of colza oil, cocoa butter, triglycerides of fatty acids containing eight to 12 carbon atoms, isopropyl myristate, petroleum oil, petrolatum, vinyl polystearate; lanolin, ricin oil, paraffin and oleyl alcohol, and a wax selected from the group consisting of microcrystalline wax and ozokerite.

5. The composition of claim 1 wherein said agent is present in an amount of 0.5 to 6 percent by weight of said composition.

6. The composition of claim 1 wherein said protective agent is present in an amount of 1–5 percent by weight of said composition.

7. The composition of claim 1 wherein said lower alcohol is ethanol.

8. The composition of claim 1 packaged under pressure in an aerosol container and including an aerosol propellant.

9. A compound having the formula

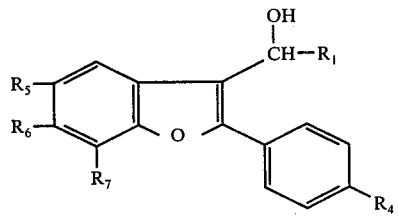

wherein
  $R_1$ is CH$_3$ and $R_4$, $R_5$, $R_6$ and $R_7$ each independently represent hydrogen or —OR$_2$ wherein $R_2$ is lower alkyl containing 1–4 carbon atoms.

* * * * *